US00PP24959P2

(12) United States Plant Patent
Beekenkamp

(10) Patent No.: US PP24,959 P2
(45) Date of Patent: Oct. 7, 2014

(54) ***BEGONIA* PLANT NAMED 'BKPBEWFER'**

(50) Latin Name: ***Begonia pendula*×*Begonia boliviensis***
Varietal Denomination: BKPBEWFER

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 119 days.

(21) Appl. No.: 13/694,136

(22) Filed: Oct. 31, 2012

(51) Int. Cl.
*A01H 5/00* (2006.01)

(52) U.S. Cl.
USPC ..... Plt./343

(58) Field of Classification Search
USPC ..... Plt./343
See application file for complete search history.

*Primary Examiner* — Wendy C Haas
(74) *Attorney, Agent, or Firm* — C. A. Whealy

(57) ABSTRACT

A new and distinct cultivar of *Begonia* plant named 'BKPBEWFER', characterized by its outwardly spreading to pendulous and mounded plant habit; freely basal branching habit; freely and continuously flowering habit; long flowering period; plants flower throughout the summer in The Netherlands; and single male and female flowers that are bright red in color.

2 Drawing Sheets

Botanical designation: *Begonia pendula*×*Begonia boliviensis*.

Cultivar denomination: 'BKPBEWFER'.

BACKGROUND OF THE INVENTION

The present invention relates to a new and distinct cultivar of *Begonia* plant, botanically known as *Begonia pendula*× *Begonia boliviensis* and hereinafter referred to by the name 'BKPBEWFER'.

The new *Begonia* plant is a product of a planned breeding program conducted by the Inventor in Maasdijk, The Netherlands. The objective of the breeding program was to develop new hanging *Begonia* plants with freely branching and flowering habit, good summer performance and long flowering period.

The new *Begonia* plant originated from a cross-pollination made by the Inventor in March, 2010 of a proprietary selection of *Begonia pendula* identified as code number 06-290-32, not patented, as the female, or seed, parent with a proprietary selection of *Begonia boliviensis* identified as code number 07-002, not patented, as the male, or pollen, parent. The new *Begonia* plant was discovered and selected by the Inventor as a single flowering plant from within the progeny of the stated cross-pollination in a controlled greenhouse environment in Maasdijk, The Netherlands in July, 2010.

Asexual reproduction of the new *Begonia* plant by tip cuttings in a controlled greenhouse environment in Maasdijk, The Netherlands since October, 2010 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEWFER'. These characteristics in combination distinguish 'BKPBEWFER' as a new and distinct *Begonia* plant:

1. Outwardly spreading to pendulous and mounded plant habit.
2. Freely basal branching habit.
3. Freely and continuously flowering habit.
4. Long flowering period; plants flower throughout the summer in The Netherlands.
5. Single male and female flowers that are bright red in color.

Plants of the new *Begonia* can be compared to plants of the female parent selection. Plants of the new *Begonia* differ primarily from plants of the female parent selection in the following characteristics:

1. Plants of the new *Begonia* have single flowers whereas plants of the female parent selection have double flowers.
2. Plants of the new *Begonia* and the female parent selection differ in flower color as plants of the female parent selection have white-colored flowers.

Plants of the new *Begonia* can be compared to plants of the male parent selection. Plants of the new *Begonia* differ primarily from plants of the male parent selection in the following characteristics:

1. Plants of the new *Begonia* have darker-colored leaves than plants of the male parent selection.
2. Plants of the new *Begonia* and the male parent selection differ in flower color as plants of the male parent selection have white-colored flowers.

Plants of the new *Begonia* can be compared to plants of *Begonia pendula*×*Begonia boliviensis* 'Encanto Orange', disclosed in U.S. Plant Pat. No. 20,898. In side-by-side comparisons conducted in Maasdijk, The Netherlands, plants of the new *Begonia* differed primarily from plants of 'Encanto Orange' in the following characteristics:

1. Plants of the new *Begonia* had darker-colored leaves than plants of 'Encanto Orange'.

2. Plants of the new *Begonia* and 'Encanto Orange' differed in flower color as plants of 'Encanto Orange' had bright orange-colored flowers.

Plants of the new *Begonia* can be compared to plants of the *Begonia* hybrid 'Sunjirared', disclosed in U.S. Plant patent application Ser. No. 13/385,537. In side-by-side comparisons conducted in Maasdijk, The Netherlands, plants of the new *Begonia* differed primarily from plants of 'Sunjirared' in the following characteristics:

1. Plants of the new *Begonia* were bushier than and not as compact as plants of 'Sunjirared'.
2. Flowers of plants of the new *Begonia* had more rounded tepal apices than flowers of plants of 'Sunjirared'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEWFER' grown in a container.

The photograph on the second sheet is a close up view of the upper and lower surfaces of typical flower buds, flowers and leaves of 'BKPBEWFER'.

DETAILED BOTANICAL DESCRIPTIONS

Plants used for the aforementioned photographs and following observations and measurements were grown in 12-cm containers during the spring and early summer in a glass-covered greenhouse in Maasdijk, The Netherlands. During the production of the plants, day temperatures ranged from 18° C. to 19° C. and night temperatures ranged from 17° C. to 18° C. Plants were seven weeks old when the photographs and the description were taken. In the following description, color references are made to The Royal Horticultural Society Colour Chart, 2007 Edition, except where general terms of ordinary dictionary significance are used.

Botanical classification: *Begonia pendula*×*Begonia boliviensis* 'BKPBEWFER'.

Parentage:

*Female, or seed, parent*.—Proprietary selection of *Begonia pendula* identified as code number 06-290-32, not patented.

*Male, or pollen, parent*.—Proprietary selection of *Begonia boliviensis* identified as code number 07-002, not patented.

Propagation:

*Type*.—By tip cuttings.

*Time to initiate roots, summer*.—About one week at temperatures ranging from 20° C. to 25° C.

*Time to initiate roots, winter*.—About one week at temperatures ranging from 18° C. to 20° C.

*Time to produce a rooted young plant, summer*.—About 32 days at temperatures ranging from 20° C. to 25° C.

*Time to produce a rooted young plant, winter*.—About 35 days at temperatures ranging from 18° C. to 20° C.

*Root description*.—Fine, fibrous; beige in color; plants of the new *Begonia* have not been observed to form tubers.

*Rooting habit*.—Freely branching; dense.

Plant description:

*Plant and growth habit*.—Outwardly spreading to pendulous and mounded plant habit; flattened globular in overall shape; freely basal branching with about nine basal branches developing per plant with lateral branches developing at potentially every node; pinching will enhance branching potential; moderately vigorous growth habit.

*Plant height*.—About 18 cm.

*Plant width*.—About 36.6 cm.

*Branch description*.—Length: About 14.4 cm. Diameter: About 7 mm. Internode length: About 3.4 cm. Texture: Smooth, glabrous. Aspect: Upright to about 40° from vertical. Strength: Outwardly bending with the weight of the leaves and flowers; flexible. Color: Close to 199A.

*Leaf description*.—Arrangement: Alternate, simple. Length: About 13.2 cm. Width: About 4.7 cm. Shape: Narrowly ovate; asymmetrical. Apex: Acuminate. Base: Oblique. Margin: Bi-serrate. Texture, upper and lower surfaces: Smooth, glabrous. Luster, upper and lower surfaces: Moderately glossy. Venation pattern: Palmate; reticulate. Color: Developing leaves, upper surface: Close to 146A. Developing leaves, lower surface: Close to 146C flushed with close to 181B. Fully expanded leaves, upper surface: Darker than between N134A and 147A; venation, close to 143A. Fully expanded leaves, lower surface: Close to 146C flushed with close to 182B; venation, close to 146A to 146B. Petioles: Length: About 2.8 cm. Diameter: About 3 mm. Texture, upper and lower surfaces: Sparsely pubescent. Color, upper and lower surfaces: Close to 146A.

*Stipules*.—Length: About 8 mm. Width: About 4 mm. Shape: Broadly ovate. Color, upper and lower surfaces: Close to 41C; venation, close to 41A.

Flower description:

*Flowering habit*.—Single rotate female and cruciform male flowers arranged in axillary compound cymes; freely flowering habit with about 135 flowers developing per plant; flowers and face mostly outwardly to drooping.

*Fragrance*.—None detected.

*Natural flowering season*.—Plants begin flowering about 38 days after planting; long flowering period, plants flower freely and continuously from spring until October in The Netherlands.

*Flower longevity*.—Individual flowers last about ten days on the plant; flowers not persistent.

*Inflorescence height*.—About 9.5 cm.

*Inflorescence diameter*.—About 9.3 cm.

*Female flowers, diameter*.—About 5.5 cm.

*Female flowers height* (*depth*).—About 5.3 cm.

*Female flowers, flower buds*.—Length: About 2.8 cm. Diameter: About 1.5 cm. Shape: Elliptic, flattened. Color: Close to 42B.

*Female flowers, tepals*.—Quantity per flower: About five in a single whorl. Length: About 4.3 cm. Width: About 1.6 cm. Shape: Elliptic to narrowly obovate. Apex: Obtuse. Margin: Entire. Texture, upper surface: Smooth, glabrous; velvety. Texture, lower surface: Smooth, glabrous; slightly velvety. Color: When opening, upper surface: Between 40A and 44B. When opening, lower surface: Close to 41A. Fully opened, upper surface: Between 40A and 44B; color does not fade with development. Fully opened, lower surface: Close to 42A to 42B; color does not fade with development.

*Female flowers, reproductive organs*.—Number of pistils per flower: About six. Pistil length: About 1 cm. Style length: About 6 mm. Style color: Close to 24C. Stigma color: Close to 15A. Ovary color: Close to 145A; wings, close to 45A.

*Male flowers, diameter*.—About 5.4 cm.

*Male flowers, height* (*depth*).—About 4.8 cm.

*Male flowers, flower buds*.—Length: About 2.1 cm. Diameter: About 1.6 cm. Shape: Broadly ovate, flattened. Color: Close to 46A; towards the base, close to 34A.

*Male flowers, tepals*.—Quantity per flower: About four in a single whorl. Length: About 4.4 cm. Width: About 1.3 cm to 3.7 cm. Shape: Two tepals are narrowly ovate and the other two are ovate. Apex: Obtuse. Margin: Entire. Texture, upper surface: Smooth, glabrous; velvety. Texture, lower surface: Smooth, glabrous; slightly velvety. Color: When opening, upper surface: Close to 44A to 44B. When opening, lower surface: Close to 42A. Fully opened, upper and lower surfaces: Close to 44A; color does not fade with development.

*Male flowers, reproductive organs*.—Number of stamens per flower: About 80. Filament length: About 4 mm. Filament color: Close to 16C to 16D. Anther length: About 2 mm. Anther shape: Club-shaped. Anther color: Close to 16A. Pollen amount: Moderate. Pollen color: Close to 11B.

*Peduncles, female and male flowers*.—Length: About 6.4 cm. Diameter: About 3 mm. Angle: About 60° from lateral branch. Strength: Weak; flexible. Texture: Smooth, glabrous. Color: Close to 152B; upper surface tinged with close to 185A.

*Pedicels, female flowers*.—Length: About 4.8 cm. Diameter: About 2 mm. Angle: About 40° from the peduncle. Strength: Weak. Texture: Smooth, glabrous. Color: Close to 145C; upper surface tinged with close to 185A.

*Pedicels, male flowers*.—Length: About 2.8 cm. Diameter: About 2 mm. Angle: Erect to about 40° from the peduncle. Strength: Weak. Texture: Smooth, glabrous. Color, upper surface: Close to 44A. Color, lower surface: Close to 145C tinged with close to 44A.

*Seeds and fruits*.—Seed and fruit production have not been observed on plants of the new *Begonia*.

Disease & pest resistance: Resistance to pathogens and pests common to *Begonia* plants has not been observed on plants of the new *Begonia*.

Temperature tolerance: Plants of the new *Begonia* have been observed to tolerate high temperature of about 35° C. and to be hardy to USDA Hardiness Zone 10.

It is claimed:

1. A new and distinct *Begonia* plant named 'BKPBEWFER' as illustrated and described.

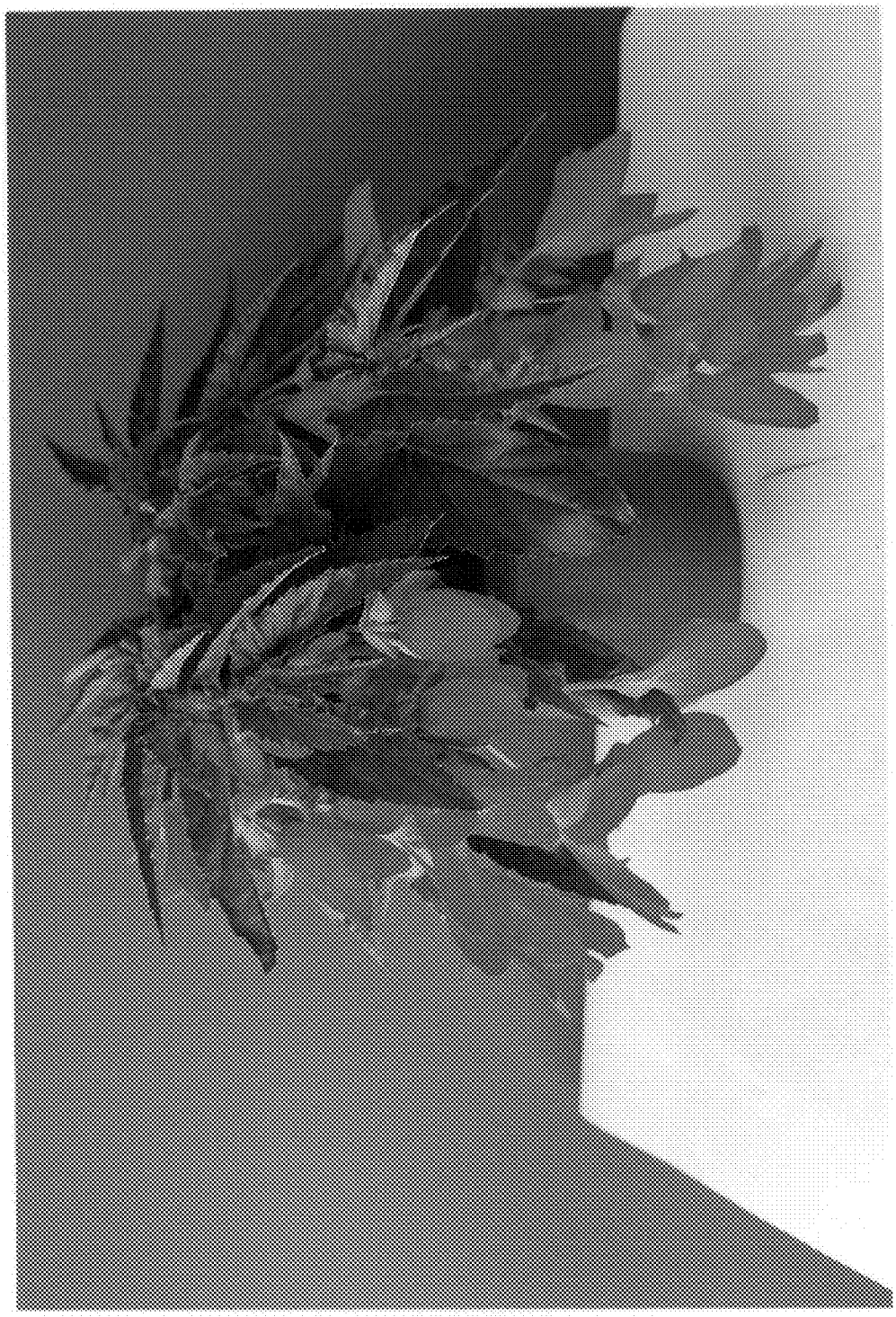

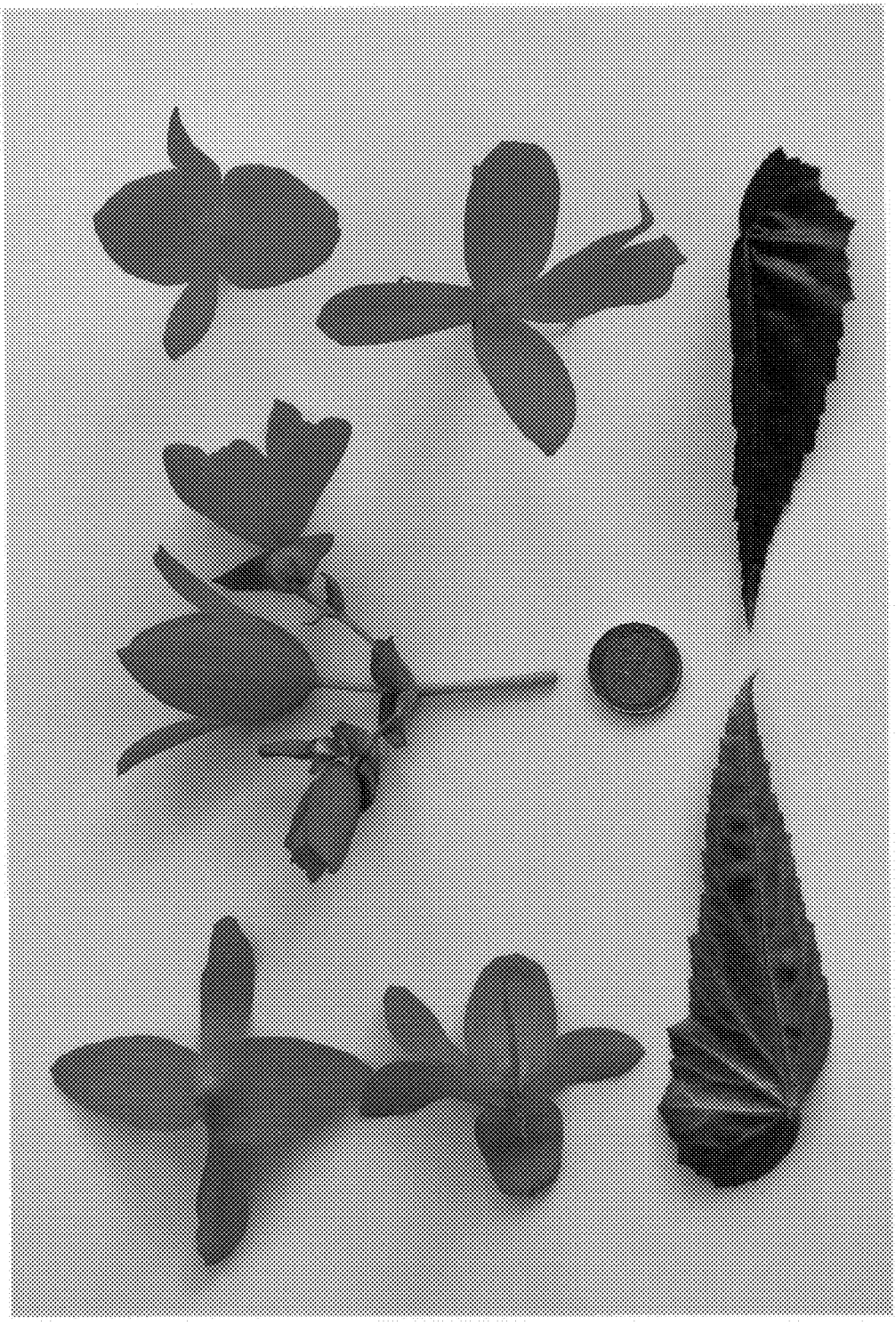

* * * * *